United States Patent
Wondka et al.

(10) Patent No.: US 8,876,791 B2
(45) Date of Patent: Nov. 4, 2014

(54) COLLATERAL PATHWAY TREATMENT USING AGENT ENTRAINED BY ASPIRATION FLOW CURRENT

(75) Inventors: Anthony Wondka, Thousand Oaks, CA (US); Peter Soltesz, Henderson, NV (US); John McCutcheon, Menlo Park, CA (US); Antony J. Fields, San Francisco, CA (US)

(73) Assignee: Pulmonx Corporation, Redwood City, CA (US)

( * ) Notice: Subject to any disclaimer, the term of this patent is extended or adjusted under 35 U.S.C. 154(b) by 495 days.

(21) Appl. No.: 12/883,039

(22) Filed: Sep. 15, 2010

(65) Prior Publication Data

US 2011/0220104 A1   Sep. 15, 2011

Related U.S. Application Data

(63) Continuation-in-part of application No. 11/620,016, filed on Jan. 4, 2007, now abandoned, and a continuation-in-part of application No. 11/067,025, filed on Feb. 25, 2005, now Pat. No. 8,206,684.

(60) Provisional application No. 60/756,732, filed on Jan. 6, 2006.

(51) Int. Cl.
| | | |
|---|---|---|
| A61M 31/00 | (2006.01) |
| A61B 17/12 | (2006.01) |
| A61M 25/10 | (2013.01) |
| A61B 17/22 | (2006.01) |
| A61B 17/00 | (2006.01) |

(52) U.S. Cl.
CPC .......... *A61M 25/10* (2013.01); *A61B 17/12104* (2013.01); *A61M 2210/1039* (2013.01); *A61B 17/12031* (2013.01); *A61B 17/12136* (2013.01); *A61B 17/1204* (2013.01); *A61B 2017/22067* (2013.01); *A61B 2017/00809* (2013.01); *A61M 2025/1052* (2013.01)
USPC ........................ 604/500; 604/509; 128/207.15

(58) Field of Classification Search
USPC ................. 604/500, 509; 128/207.15, 207.14
See application file for complete search history.

(56) References Cited

U.S. PATENT DOCUMENTS

| | | | |
|---|---|---|---|
| 2,981,254 A | 4/1961 | Vanderbilt |
| 3,322,126 A | 5/1967 | Rusch et al. |

(Continued)

FOREIGN PATENT DOCUMENTS

| | | |
|---|---|---|
| DE | 92057497.7 U1 | 6/1992 |
| EP | 0 692 273 | 1/1996 |

(Continued)

OTHER PUBLICATIONS

Al Jishi et al., "Selective Bronchial Occlusion for Treatment of Bullous Interstitial Emphysema and Bronchopleural Fistula." J Pediatric Surgery, 1994; 29:1545-1547.

(Continued)

*Primary Examiner* — Edelmira Bosques
(74) *Attorney, Agent, or Firm* — Wilson Sonsini Goodrich & Rosati

(57) ABSTRACT

A method and system for increasing the flow resistance of collateral pathways in the lung by employing aspiration to establish an artificial convective flow current between compartments in the lung in order to entrain and deliver a clogging agent preferentially to the collateral pathways. The method may sometimes be performed after lung has been assessed for the presence of collateral pathways.

8 Claims, 9 Drawing Sheets

(56) References Cited

U.S. PATENT DOCUMENTS

| | | |
|---|---|---|
| 3,498,286 A | 3/1970 | Polanyi et al. |
| 3,657,744 A | 4/1972 | Ersek |
| 3,669,098 A | 6/1972 | Takahashi |
| 3,677,262 A | 7/1972 | Zukowski |
| 3,776,222 A | 12/1973 | Smiddy |
| 3,788,327 A | 1/1974 | Donowitz et al. |
| 3,866,599 A | 2/1975 | Johnson |
| 3,874,388 A | 4/1975 | King et al. |
| 3,913,568 A | 10/1975 | Carpenter |
| 4,014,318 A | 3/1977 | Dockum et al. |
| 4,031,885 A | 6/1977 | Davis et al. |
| 4,041,936 A | 8/1977 | Carden |
| 4,086,665 A | 5/1978 | Poirier |
| 4,212,463 A | 7/1980 | Repinski et al. |
| 4,250,873 A | 2/1981 | Bonnet |
| 4,302,854 A | 12/1981 | Runge |
| 4,327,720 A | 5/1982 | Bronson et al. |
| 4,327,721 A | 5/1982 | Goldin et al. |
| 4,413,632 A | 11/1983 | Schlessinger et al. |
| 4,453,545 A | 6/1984 | Inoue |
| 4,468,216 A | 8/1984 | Muto |
| 4,477,930 A | 10/1984 | Totten et al. |
| 4,567,882 A | 2/1986 | Heller |
| 4,710,192 A | 12/1987 | Liotta et al. |
| 4,716,896 A | 1/1988 | Ackerman |
| 4,732,152 A | 3/1988 | Wallsten et al. |
| 4,742,819 A | 5/1988 | George |
| 4,759,758 A | 7/1988 | Gabbay |
| 4,784,133 A | 11/1988 | Mackin |
| 4,795,449 A | 1/1989 | Schneider et al. |
| 4,796,639 A | 1/1989 | Snow et al. |
| 4,808,183 A | 2/1989 | Panje |
| 4,819,664 A | 4/1989 | Nazari |
| 4,830,003 A | 5/1989 | Wolff et al. |
| 4,832,680 A | 5/1989 | Haber et al. |
| 4,846,153 A | 7/1989 | Berci |
| 4,846,836 A | 7/1989 | Reich |
| 4,850,371 A | 7/1989 | Broadhurst et al. |
| 4,850,999 A | 7/1989 | Planck |
| 4,852,568 A | 8/1989 | Kensey |
| 4,862,874 A | 9/1989 | Kellner |
| 4,877,025 A | 10/1989 | Hanson |
| 4,896,941 A | 1/1990 | Hayashi et al. |
| 4,934,999 A | 6/1990 | Bader |
| 4,949,716 A | 8/1990 | Chenoweth |
| 4,955,375 A | 9/1990 | Martinez |
| 4,958,932 A | 9/1990 | Kegelman et al. |
| 4,961,738 A | 10/1990 | Mackin |
| 4,968,294 A | 11/1990 | Salama |
| 4,972,842 A | 11/1990 | Korten et al. |
| 4,976,710 A | 12/1990 | Mackin |
| 5,056,529 A | 10/1991 | de Groot |
| 5,061,274 A | 10/1991 | Kensey |
| 5,116,360 A | 5/1992 | Pinchuk et al. |
| 5,116,564 A | 5/1992 | Jansen et al. |
| 5,123,919 A | 6/1992 | Sauter et al. |
| 5,143,062 A | 9/1992 | Peckham |
| 5,146,916 A | 9/1992 | Catalani |
| 5,151,105 A | 9/1992 | Kwan-Gett |
| 5,161,524 A | 11/1992 | Evans |
| 5,246,012 A | 9/1993 | Strickland |
| 5,285,778 A | 2/1994 | Mackin |
| 5,306,234 A | 4/1994 | Johnson |
| 5,309,903 A | 5/1994 | Long |
| 5,331,947 A | 7/1994 | Shturman |
| 5,352,240 A | 10/1994 | Ross |
| 5,358,518 A | 10/1994 | Camilli |
| 5,361,753 A | 11/1994 | Pothmann et al. |
| 5,392,775 A | 2/1995 | Adkins et al. |
| 5,409,019 A | 4/1995 | Wilk |
| 5,411,507 A | 5/1995 | Heckele |
| 5,411,552 A | 5/1995 | Andersen et al. |
| 5,413,599 A | 5/1995 | Imachi et al. |
| 5,417,226 A | 5/1995 | Juma |
| 5,445,626 A | 8/1995 | Gigante |
| 5,447,165 A | 9/1995 | Gustafss |
| 5,477,851 A | 12/1995 | Callaghan et al. |
| 5,486,154 A | 1/1996 | Kelleher |
| 5,499,625 A | 3/1996 | Frass et al. |
| 5,499,995 A | 3/1996 | Teirstein |
| 5,500,014 A | 3/1996 | Quijano et al. |
| 5,562,608 A | 10/1996 | Sekins et al. |
| 5,598,840 A | 2/1997 | Iund et al. |
| 5,642,730 A | 7/1997 | Baran |
| 5,645,519 A | 7/1997 | Lee et al. |
| 5,645,565 A | 7/1997 | Rudd et al. |
| 5,653,231 A | 8/1997 | Bell |
| 5,660,175 A | 8/1997 | Dayal |
| 5,662,713 A | 9/1997 | Andersen et al. |
| 5,682,880 A | 11/1997 | Brain |
| 5,683,451 A | 11/1997 | Lenker et al. |
| 5,697,968 A | 12/1997 | Rogers et al. |
| 5,707,352 A | 1/1998 | Sekins et al. |
| 5,752,921 A | 5/1998 | Orr |
| 5,755,770 A | 5/1998 | Ravenscroft |
| 5,757,593 A | 5/1998 | Stoger |
| 5,800,339 A | 9/1998 | Salama |
| 5,840,081 A | 11/1998 | Andersen et al. |
| 5,851,232 A | 12/1998 | Lois |
| 5,855,587 A | 1/1999 | Hyon et al. |
| 5,855,597 A | 1/1999 | Jayaraman |
| 5,855,601 A | 1/1999 | Bessler et al. |
| 5,893,867 A | 4/1999 | Bagaoisan et al. |
| 5,944,738 A | 8/1999 | Amplatz et al. |
| 5,947,997 A | 9/1999 | Pavcnik et al. |
| 5,954,050 A | 9/1999 | Christopher |
| 5,954,766 A | 9/1999 | Zadno-Azizi et al. |
| 5,957,919 A | 9/1999 | Laufer |
| 5,957,949 A | 9/1999 | Leonhardt et al. |
| 5,972,026 A | 10/1999 | Laufer et al. |
| 5,976,174 A | 11/1999 | Ruiz |
| 5,984,965 A | 11/1999 | Knapp et al. |
| 6,007,575 A | 12/1999 | Samuels |
| 6,009,614 A | 1/2000 | Morales |
| 6,016,839 A | 1/2000 | Raftis et al. |
| 6,020,380 A | 2/2000 | Killian |
| 6,022,312 A | 2/2000 | Chaussy et al. |
| 6,027,525 A | 2/2000 | Suh et al. |
| 6,050,972 A | 4/2000 | Zadno-Azizi et al. |
| 6,051,022 A | 4/2000 | Cai et al. |
| 6,068,602 A | 5/2000 | Tham et al. |
| 6,068,635 A | 5/2000 | Gianotti |
| 6,068,638 A | 5/2000 | Makower |
| 6,071,237 A | 6/2000 | Weil et al. |
| 6,077,291 A | 6/2000 | Das |
| 6,083,255 A | 7/2000 | Laufer et al. |
| 6,123,663 A | 9/2000 | Rebuffat |
| 6,135,729 A | 10/2000 | Aber |
| 6,135,991 A | 10/2000 | Muni et al. |
| 6,141,855 A | 11/2000 | Morales |
| 6,162,245 A | 12/2000 | Jayaraman |
| 6,168,614 B1 | 1/2001 | Andersen et al. |
| 6,174,323 B1 | 1/2001 | Biggs et al. |
| 6,174,331 B1 | 1/2001 | Moe et al. |
| 6,183,520 B1 | 2/2001 | Pintauro et al. |
| 6,200,333 B1 | 3/2001 | Laufer |
| 6,206,918 B1 | 3/2001 | Campbell et al. |
| 6,234,996 B1 | 5/2001 | Bagaoisan et al. |
| 6,240,615 B1 | 6/2001 | Kimes et al. |
| 6,245,102 B1 | 6/2001 | Jayaraman |
| 6,258,100 B1 | 7/2001 | Alferness et al. |
| 6,270,527 B1 | 8/2001 | Campbell et al. |
| 6,283,988 B1 | 9/2001 | Laufer et al. |
| 6,287,290 B1 | 9/2001 | Perkins et al. |
| 6,293,951 B1 | 9/2001 | Alferness et al. |
| 6,302,893 B1 | 10/2001 | Limon et al. |
| 6,312,407 B1 | 11/2001 | Zadno-Azizi et al. |
| 6,325,777 B1 | 12/2001 | Zadno-Azizi et al. |
| 6,325,778 B1 | 12/2001 | Zadno-Azizi et al. |
| 6,327,772 B1 | 12/2001 | Zadno-Azizi et al. |
| 6,328,689 B1 | 12/2001 | Gonzalez |
| 6,355,014 B1 | 3/2002 | Zadno-Azizi et al. |
| 6,398,775 B1 | 6/2002 | Perkins et al. |
| 6,402,754 B1 | 6/2002 | Gonzalez |

(56) References Cited

U.S. PATENT DOCUMENTS

| | | |
|---|---|---|
| 6,416,554 B1 | 7/2002 | Alferness et al. |
| 6,450,976 B2 | 9/2002 | Korotko et al. |
| 6,458,076 B1 | 10/2002 | Pruitt |
| 6,458,153 B1 | 10/2002 | Bailey et al. |
| 6,485,407 B2 | 11/2002 | Alferness et al. |
| 6,488,673 B1 | 12/2002 | Laufer et al. |
| 6,491,706 B1 | 12/2002 | Alferness et al. |
| 6,493,589 B1 | 12/2002 | Medhkour et al. |
| 6,510,846 B1 | 1/2003 | O'Rourke |
| 6,527,761 B1 | 3/2003 | Soltesz et al. |
| 6,558,418 B2 | 5/2003 | Carpentier et al. |
| 6,568,387 B2 | 5/2003 | Davenport et al. |
| 6,585,639 B1 | 7/2003 | Kotmel et al. |
| 6,599,311 B1 | 7/2003 | Biggs et al. |
| 6,610,043 B1 | 8/2003 | Ingenito |
| 6,629,951 B2 | 10/2003 | Laufer et al. |
| 6,632,980 B1 | 10/2003 | Yadav et al. |
| 6,653,525 B2 | 11/2003 | Ingenito et al. |
| 6,679,264 B1 | 1/2004 | Deem et al. |
| 6,692,494 B1 | 2/2004 | Cooper et al. |
| 6,709,401 B2 | 3/2004 | Perkins et al. |
| 6,709,427 B1 | 3/2004 | Nash et al. |
| 6,712,812 B2 | 3/2004 | Roschak et al. |
| 6,722,360 B2 | 4/2004 | Doshi |
| 6,726,598 B1 | 4/2004 | Jarvis et al. |
| 6,743,259 B2 | 6/2004 | Ginn |
| 6,749,606 B2 | 6/2004 | Keast et al. |
| 6,787,141 B1 | 9/2004 | Melvin et al. |
| 6,878,141 B1 | 4/2005 | Perkins et al. |
| 6,886,558 B2 | 5/2005 | Tanaka |
| 6,997,189 B2 | 2/2006 | Biggs et al. |
| 7,011,094 B2 | 3/2006 | Rapacki et al. |
| 7,022,088 B2 | 4/2006 | Keast et al. |
| 7,086,398 B2 | 8/2006 | Tanaka |
| 7,100,616 B2 | 9/2006 | Springmeyer |
| 7,175,644 B2 | 2/2007 | Cooper et al. |
| 7,186,259 B2 | 3/2007 | Perkins et al. |
| 7,252,086 B2 | 8/2007 | Tanaka |
| 7,412,977 B2 | 8/2008 | Fields et al. |
| 7,588,033 B2 | 9/2009 | Wondka |
| 7,670,373 B1 | 3/2010 | Sabanathan |
| 2001/0016704 A1 | 8/2001 | Zadno-Azizi et al. |
| 2001/0025132 A1 | 9/2001 | Alferness et al. |
| 2001/0041906 A1 | 11/2001 | Gonzalez |
| 2001/0051799 A1 | 12/2001 | Ingenito |
| 2001/0052344 A1 | 12/2001 | Doshi |
| 2001/0056274 A1 | 12/2001 | Perkins et al. |
| 2002/0007831 A1 | 1/2002 | Davenport et al. |
| 2002/0026233 A1 | 2/2002 | Shaknovich |
| 2002/0049370 A1 | 4/2002 | Laufer et al. |
| 2002/0062120 A1 | 5/2002 | Perkins et al. |
| 2002/0077593 A1 | 6/2002 | Perkins et al. |
| 2002/0077696 A1 | 6/2002 | Zadno-Azizi et al. |
| 2002/0087153 A1 | 7/2002 | Roschak et al. |
| 2002/0095209 A1 | 7/2002 | Zadno-Azizi et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0138135 A1 | 9/2002 | Duerig et al. |
| 2002/0147462 A1 | 10/2002 | Mair et al. |
| 2003/0018327 A1 | 1/2003 | Truckai et al. |
| 2003/0018344 A1 | 1/2003 | Kaji et al. |
| 2003/0050648 A1 | 3/2003 | Alferness et al. |
| 2003/0051733 A1 | 3/2003 | Kotmel et al. |
| 2003/0083671 A1 | 5/2003 | Rimbaugh et al. |
| 2003/0164168 A1 | 9/2003 | Shaw |
| 2003/0181922 A1 | 9/2003 | Alferness |
| 2003/0183235 A1 | 10/2003 | Rimbaugh et al. |
| 2003/0195385 A1 | 10/2003 | DeVore |
| 2003/0228344 A1 | 12/2003 | Fields et al. |
| 2004/0073155 A1 | 4/2004 | Laufer et al. |
| 2004/0073201 A1 | 4/2004 | Cooper et al. |
| 2004/0093075 A1 | 5/2004 | Kuehne |
| 2004/0158228 A1 | 8/2004 | Perkins et al. |
| 2004/0220556 A1 | 11/2004 | Cooper et al. |
| 2004/0244802 A1 | 12/2004 | Tanaka |
| 2005/0196344 A1 | 9/2005 | McCutcheon et al. |
| 2006/0200076 A1 | 9/2006 | Gonzalez et al. |
| 2006/0264772 A1 | 11/2006 | Aljuri et al. |
| 2007/0186932 A1 | 8/2007 | Wondka et al. |

FOREIGN PATENT DOCUMENTS

| | | |
|---|---|---|
| EP | 0 621 015 B1 | 3/1998 |
| EP | 1 078 601 A2 | 2/2001 |
| EP | 1 151 729 A1 | 11/2001 |
| GB | 2324729 A | 11/1998 |
| RU | 2140211 C1 | 10/1999 |
| SU | 852321 A1 | 7/1981 |
| SU | 1371700 A1 | 2/1988 |
| SU | 1593651 A1 | 9/1990 |
| WO | WO 94/26175 A1 | 11/1994 |
| WO | WO 95/33506 | 12/1995 |
| WO | WO 97/44085 A2 | 11/1997 |
| WO | WO 98/00840 A1 | 1/1998 |
| WO | WO 98/39047 A1 | 9/1998 |
| WO | WO 98/44854 A1 | 10/1998 |
| WO | WO 99/42059 A2 | 8/1999 |
| WO | WO 99/64109 A1 | 12/1999 |
| WO | WO 00/15149 A1 | 3/2000 |
| WO | WO 00/62699 A2 | 10/2000 |
| WO | WO 01/10314 A2 | 2/2001 |
| WO | WO 01/12104 A1 | 2/2001 |
| WO | WO 01/45590 A2 | 6/2001 |
| WO | WO 01/54585 A1 | 8/2001 |
| WO | WO 01/54625 A1 | 8/2001 |
| WO | WO 01/54685 A1 | 8/2001 |
| WO | WO 01/74271 A1 | 10/2001 |
| WO | WO 02/32333 A1 | 4/2002 |
| WO | WO 02/064045 A1 | 8/2002 |
| WO | WO 02/064190 A2 | 8/2002 |
| WO | WO 02/069823 A2 | 9/2002 |
| WO | WO 03/079944 A1 | 10/2003 |
| WO | WO 03/088820 A2 | 10/2003 |
| WO | WO 2006/078451 A2 | 7/2006 |

OTHER PUBLICATIONS

Autocath.RTM. 100—Nonsurgical, Intraurethral Bladder Control Device for Incontinent and Retentive Women—Dr. Kulisz's Development, retrieved from the Internet: <http://www.kulisz.com/autocath.htm> on Oct. 22, 2009.

Becker et al., "Lung Volumes Before and After Lung Volume Reduction Surgery," Am J Respir Crit Care Med, May 1998;157(5 Pt 1):1593-9.

Burger et al., "Gas exchange in the parabronchial lung of birds: Experiments in unidirectionally ventilated ducks," Respiration Physiology Mar. 1979; 36(1):19-37.

Cohn et al., Novel reverse thernnoresponsiye injectable poly(ether carbonates)s, J Mater Sci Mater Med. Feb. 2003;14(2):175-80.

Cotran et al., Chaper 15 in *Robbins Pathologic Basis of Disease*, 5th edition, eds., W.B. Saunders Company, Philadelphia, 1974 p. 683-694.

Criner et al., "Effect of Lung Volume Reduction Surgery on Diaphragm Strength," *Am J Respir Crit Care Med*, May 1998;157(5 Pt 1):1578-85.

Gonzalez et al., [Abstract] "Should patients undergoing a bronchoscopy be sedated?" Acta Anaesthesiol Scand. Apr. 2003;47(4):411-5.

Harada et al., "Re-expansion of Refractory Atelectasis Using a Bronchofiberscope with a Balloon Cuff," Chest. Dec. 1983;84(6):725-8.

Harris et al., "The Experimental Production in Dogs of Emphysema with Associated Asthmatic Syndrome by Means of an Intratracheal Ball Valve," J. Lab. Clini. Med., 1919; 9(iv):75-88.

Institute for Clinical Evaluative Sciences (ICES), "Endotracheal tube choice," 2001; retrieved from the Internet: <http://www.ices.on.ca/informed/periodical/subissue/133-ip7422.pdf>.

Kotloff et al., "Comparison of Short-term Functional Outcomes Following Unilateral and Bilateral Lung Volume Reduction Surgery," Chest. Apr. 1998;113(4):890-5.

(56) References Cited

OTHER PUBLICATIONS

Lewis et al., "Pulmonary Interstitial Emphysema: Selective Broncial Occlusion with a Swan—Ganz Catheter", Archives of Disease in Childhood, 1988; 63:313-315.

Mathew et al., "Selective bronchial obstruction for treatment of bullous interstitial emphysema." J. of Ped., 1980; 96:475-477.

Morrell et al., "Collateral ventilation and gas exchange during airway occlusion in the normal human lung," Am Rev Respir Dis. Mar. 1993;147(3):535-539.

Ojo et al., "Lung Volume Reduction Surgery Alters Management of Pulmonary Nodules in Patients With Severe COPD," Chest. Dec. 1997;112(6):1494-500.

Okada et al., "Emergent Bronchofiberoptic Bronchial Occlusion for Intractable Pneumothorax with Severe Emphysema", Jpn J Thorac Cardiovasc Surg. Nov. 1998;46(11):1078-81.

Puhakka et al., "Acute Bronchial Obstruction: An Experimental Rabbit Model Study", Int. J. of Pediatric Otorhinolaryngology, 1989; 18:107-118.

Raasch et al., "Radiographic Anatomy of the Interlobar Fissure: A Study of r100 Specimens," AJR 1982; 138:1043-1049.

Sclafani, "Clearing the Airways," *AARC Times*, Jan. 1999, pp. 69-72.

Snider et al., "The Definition of Emphysema: Report of the National Heart Lung and Blood Institute, Division of Lung Diseases Workshop," Am. Rev. Respir. Dis. 1985; 132:182-185.

Woodring et al., "Pneumothorax ex Vacuo", Chest, 1996; 100:1102-1105.

Woolcock et al., "Mechanical Factors Influencing Collateral Ventilation in Human, Dog, and Pig Lungs," J. Appl Physiol. Jan. 1971;30(1):99-115.

Office action dated Jan. 14, 2010 for U.S. Appl. No. 11/620,016.

Office action dated Jul. 2, 2010 for U.S. Appl. No. 11/620,016.

COLLATERAL PATHWAY TREATMENT USING AGENT ENTRAINED BY ASPIRATION FLOW CURRENT

CROSS-REFERENCES TO RELATED APPLICATIONS

The present application is a continuation-in-part and claims the benefit of U.S. patent application Ser. No. 11/067,025, entitled Methods and Devices for Blocking Flow Through Collateral Pathways in the Lung, filed Feb. 25, 2005, which claims the benefit of Provisional U.S. Application No. 60/548,791, filed Feb. 27, 2004. The present application is also a continuation-in-part and claims the benefit of U.S. patent application Ser. No. 11/620,016, entitled Collateral Pathway Treatment Using Agent Entrained by Aspiration Flow Current, which claims the benefit of Provisional U.S. Application No. 60/756,732, filed Jan. 6, 2006. The full disclosures of all of the references mentioned above are hereby incorporated herein by reference.

BACKGROUND OF THE INVENTION

The subject invention relates to performing catheter-based diagnostic or therapeutic procedures within the lung. In particular, the invention relates to closing or partially closing intercommunicating channels within the lung in order to prevent a target lung compartment from receiving collateral ventilation through such intercommunicating secondary channels.

The lung consists of a left lung and right lung having two and three lobes respectively (FIG. 1). Air is delivered into and out of the lobes of the lungs through a bronchial system comprising tubular airways starting with the trachea which divides and subdivides until the airways reach the periphery of the lobes terminating in long lobules which contain the alveoli. In a normal lung, the tissue of each lobe is physically separated from that of other lobes, the separation being referred to as a fissure. This fissure prevents the passage of air between neighboring lobes. However, for reasons not fully understood, the fissures separating the lobes are sometimes absent or incomplete, allowing the collateral flow of air between neighboring lobes. At the periphery of a given lobe within the lung, there exist channels or pores that interconnect alveoli or terminal bronchioles from one bronchial tree branch to the alveoli or terminal bronchioles belonging to the neighboring bronchial tree branch.

In some disease states, such interconnections at the lung lobule level and/or connections through incomplete fissures can become more pronounced, rendering certain treatments problematic. For example, emphysema may be treated by minimally invasive lung volume reduction (LVR) where feeding airways that deliver air to diseased hyperinflated lung lobes or segments within a lobe are plugged or otherwise occluded to prevent re-inflation. However, if collateral interconnections exist, LVR can be hampered since the collapsed region can re-inflate through any collateral connection.

Proposed treatments to circumvent this problem include permanently shrinking the targeted region, lobe or lobe segment, such as by ablating, heating, mechanically compressing with an implant, or the like. In such treatments, collateral leakage is immaterial since reinflation of the treated area is physically prevented by nature of the treatment. These treatments, however, are destructive and have not yet achieved good, safe results and are considered undesirable.

Therefore, in the case of minimally invasive lung volume reduction for emphysema treatment it would be desirable to partially or completely block or close collateral passages and pathways which allow collateral ventilation with adjacent regions.

One such method is described in published US Patent Application 2003/0228344 which proposes injecting an agent bronchscopically, transthoracically or by puncturing a bronchial wall, to close the collateral channels while using a one-way valve in an airway to control the air flow path so that the deposition of the agent is directed into the collateral channels. Unfortunately, this technique has a significant disadvantage in that the targeting of the agent is poorly controlled with the methods they describe. Pressure differentials, created by use of a bronchial one-way valve or applying vacuum transthoracically to a lung area, allow the agent to mix and spread to unwanted areas. An additional disadvantage of this technique is that the user must perform lung volume reduction on the patient by implanting bronchial valves or occluders in order to diagnose whether or not the patient possess collateral channels. If the patient does not develop lung area deflation by gas absorption, or absorption atelectasis, then it is concluded there are collateral channels and the patient requires the collateral channel treatment. This is a very inconvenient treatment protocol.

As will be described in the subsequent sections, the present invention solves at least some of the deficiencies of such prior art techniques.

BRIEF SUMMARY OF THE INVENTION

The present invention provides methods and devices for partially or completely closing collateral pathways in lungs, including between and within individual lobes. In particular, the methods comprise isolating a target lung region (TLR) with an isolation catheter, applying vacuum to the target area via the catheter to establish a convective flow current from a neighboring lung compartment (NLC) through the collateral pathway (if any) into the isolated target area and the catheter and out the body. If collateral flow exists, an agent is delivered into the neighboring lung compartment, typically using a catheter or other delivery device introduced through the bronchial tree and into the neighboring lung compartment. The agent is entrained into the convective flow current through the collateral pathway(s) established by the vacuum. The entrained substance enters and lodges in the collateral pathway(s), while excess agent remains entrained with the convective flow current through the collateral pathway and is typically conducted out of the body through the aspiration catheter.

DETAILED DESCRIPTION OF THE INVENTION

Figure 1:
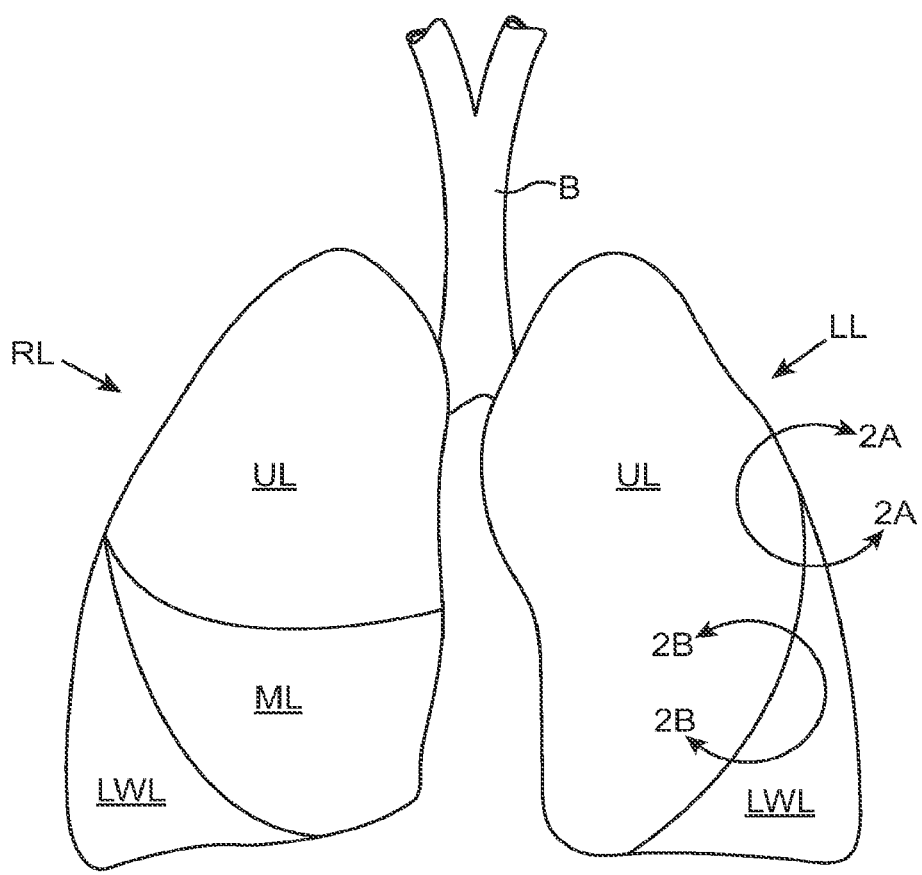
FIG. 1 illustrates the lobes of a lung.

Referring now to FIG. 1, the respiratory system of the patient starts at the mouth and extends through the vocal cords and into the trachea where it then joins the main stem bronchi B which leads into the right lung RL and the left lung LL. The bronchi going into the right lung divide into the three lobar bronchi which lead into the upper lobe UL, the middle lobe ML and the lower lobe LWL. The lobes of the right lung each include ten segments which are discrete units of the lung separated from each other by a fibrous septum generally referred to as a lung wall. The left lung LL includes only an upper lobe UL and a lower lobe LWL, where the individual lobes include eight or nine segments.

Each lung segment, also referred to as a bronchopulmonary segment, is an anatomically distinct unit or compartment of the lung which is fed air by a tertiary bronchus and which oxygenates blood through a tertiary artery. Normally, the lung segment and its surrounding fibrous septum are intact units which can be surgically removed or separated from the remainder of the lung without interrupting the function of the surrounding lung segments.

The presence of collateral flow channels in the fibrous septum or wall of a diseased lung segment is problematic since the diseased segment cannot be removed or even isolated successfully with the collateral channels intact. In the case of isolation and deflation of the diseased lung segment, the presence of the collateral channels will permit the reentry of air as the patient breathes. Thus, the present invention, by occluding the collateral passages, returns a perforate or porous lung wall into a functionally intact lung wall which permits subsequent treatment of diseased regions using endobronchial or other treatment protocols.

Figure 2A:
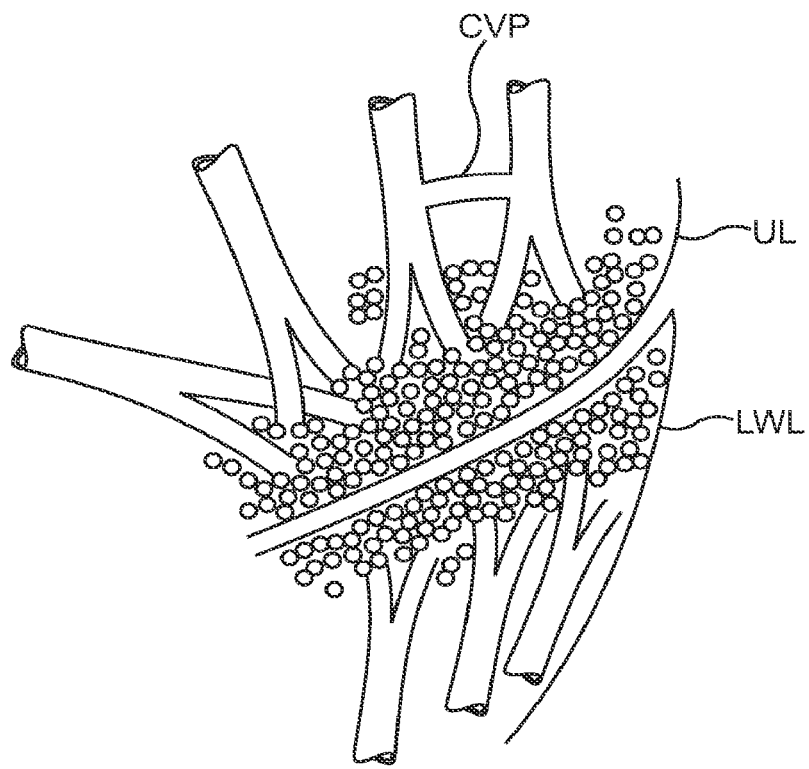
FIGS. 2A and 2B illustrate a lung lobule collateral pathway and an incomplete lobar fissure collateral pathway, respectively.
Figure 2B:
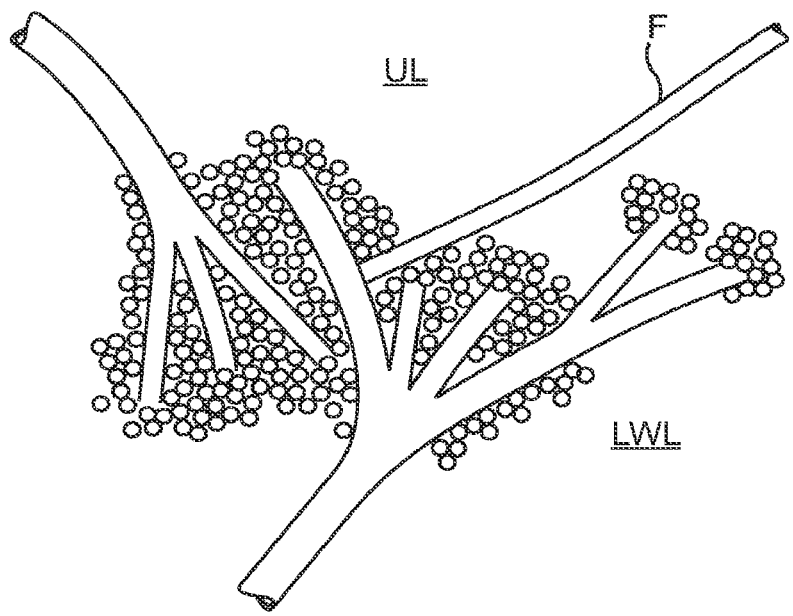

FIGS. 2A and 2B illustrate a collateral ventilation pathway (CVP) in a lung, including the pores of Kahn, Lambert's canals, and Martin's channels. These pathways permit cross communication between segments within a lobe. It has been hypothesized that in the presence of emphysema and a missing lobar fissure, these structures allow cross communication from a segment of one lobe to a segment of a neighboring lobe, as shown in FIG. 2A. FIG. 2B describes an incomplete fissure F between two lobes as an example of airway incursion from one lobe UL to another LWL. The airway incursion effectively connects the bronchial trees from neighboring lobes collaterally.

According to one embodiment of the present invention, the patient is usually diagnosed for the presence or absence of collateral ventilation (CV), typically using a minimally invasive catheter-based spirometry test described in co-pending application Ser. No. 11/296,951, the full disclosure of which is incorporated herein by reference. The test requires only a simple benign catheterization procedure. Usually, the patient is further diagnosed, using a minimally invasive catheter-based procedure to determine which area of the lung is most diseased and in most need of treatment, e.g., as described in U.S. patent Ser. No. 10/241,733, the full disclosure of which is incorporated herein by reference. Performing these diagnostic tests pre-operatively will help assure that the collateral channel treatment is performed in a lung area that is free from problematic collateral pathways and which can benefit from the treatment.

Collateral channels may have beneficial effects in emphysematic patients such as limitation of hyperinflation, minimization of bullae formation, and reduce flow limitation during exhalation. Therefore, when closing the collateral channels, the risk has to be offset by the benefit. In the present invention, since the lung area is preferably first diagnosed as an area that can benefit by being collapsed by the lung volume reduction procedure, the benefit of closing the collateral channels is more likely to offset the risk of closing these channels.

Referring to FIGS. 3A-3D, a first embodiment of the invention is described. The lung area targeted for therapy is first isolated with a balloon catheter 10 (FIG. 3A), henceforth referred to as the aspiration catheter, which is inserted through the mouth and the main bronchus B and into the tracheobronchial tree, optionally using a bronchoscope or other delivery tube or sheath (not shown). The target lung area can be in the lobar bronchus, the segmental bronchus or even deeper into the bronchial tree, depending on what the needs of the therapy are and where the targeted lung bronchopulmonary compartment, henceforth referred to as the target lung region (TLR), is located. Isolation is created usually by inflating a balloon or cuff 12 at the tip of the catheter which seals the annular space between the catheter and the bronchus wall. A lumen extends the length of the catheter providing access to the targeted lung region (TLR). The proximal end of the catheter 10 outside the patient's body is coupled to an instrument 14, typically a pump or a vacuum source, which provides vacuum, described in more detail below. The aspiration catheter 10 can be insertable through a bronchoscope working channel, or can be configured to be placed onto the outside of a bronchoscope, in which case the bronchoscope instrument channel can be used for the applying vacuum to the targeted region, although there are several other possible configurations.

Figure 3A:
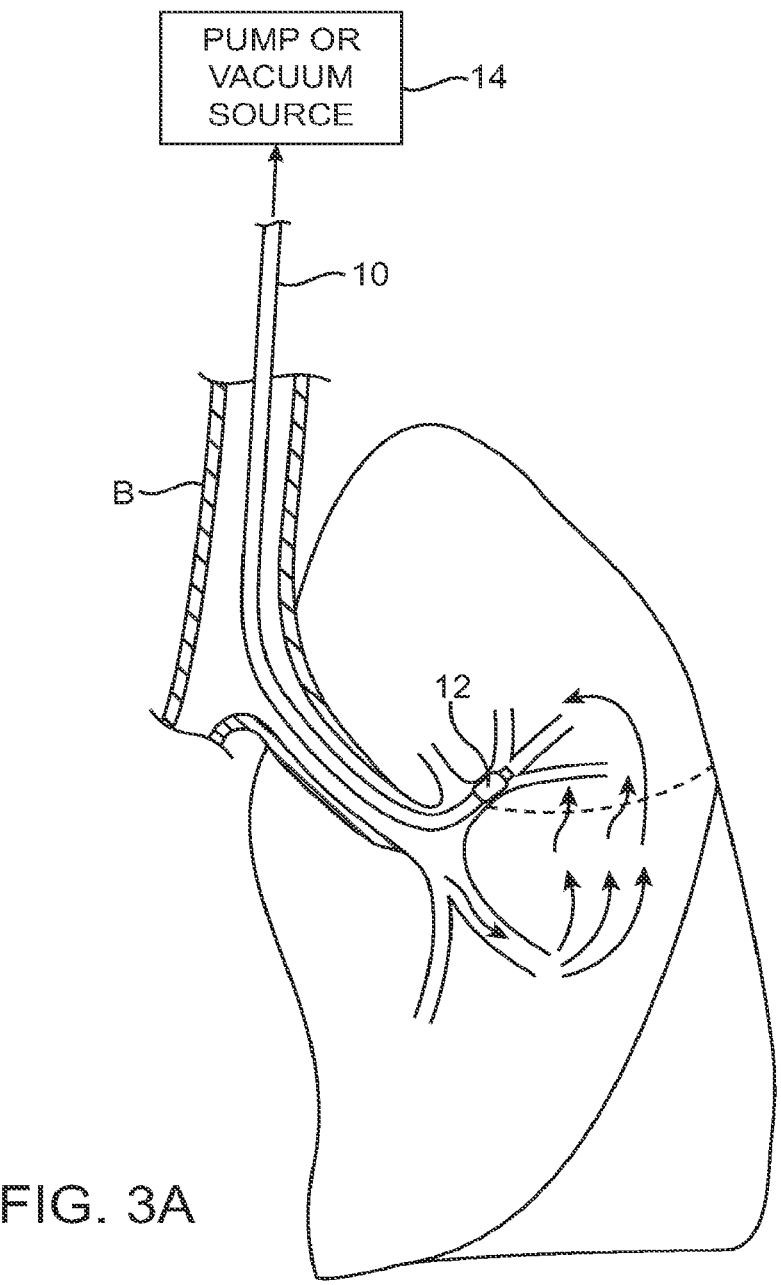
FIGS. 3A-3D illustrate an exemplary method and procedure in accordance with the principles of the present invention.
Figure 3B:
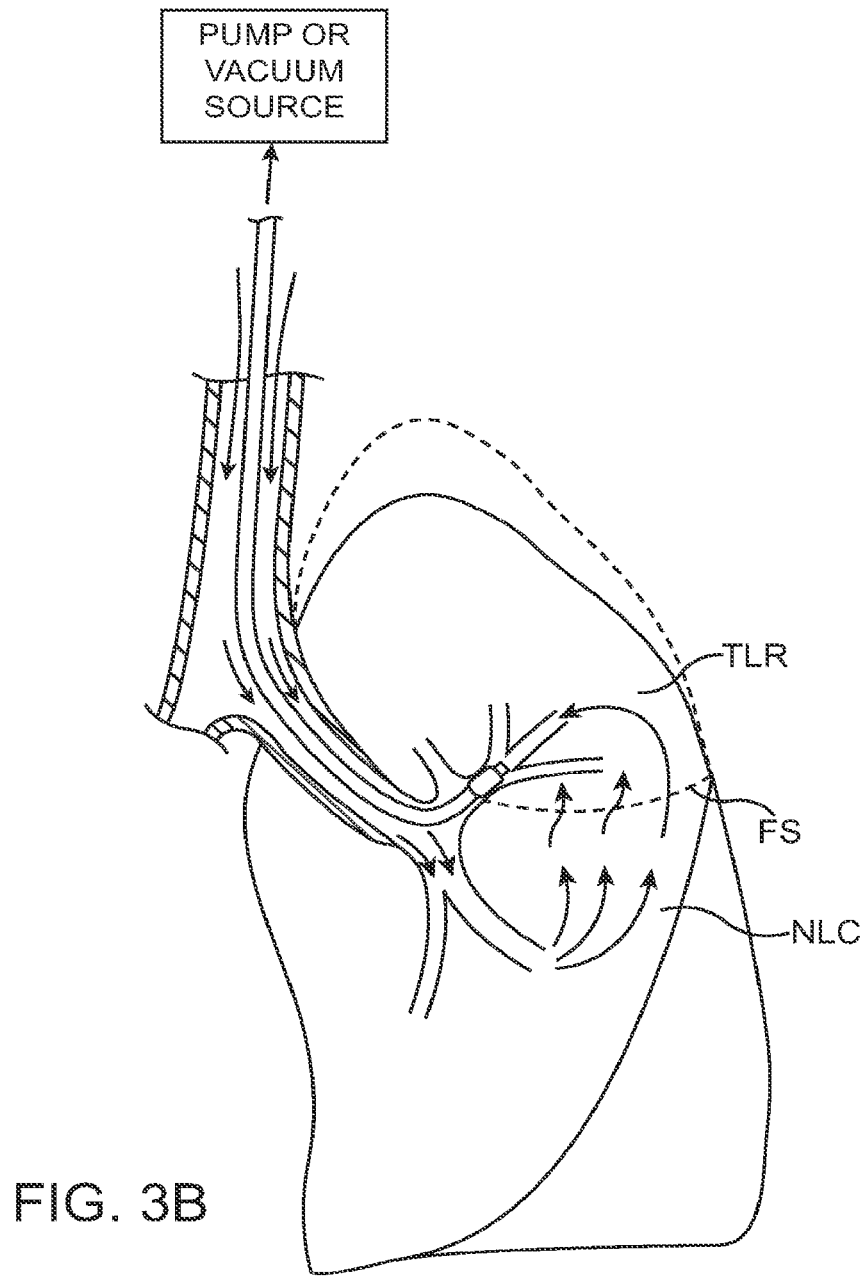

Referring to FIG. 3B, vacuum supplied by the instrument 14 is applied to the target lung region (TLR) via the aspiration catheter 10. Initially when the vacuum is applied, the pressure in the bronchi of the targeted lung region (TLR) is reduced (the broken line represents the original lung size). The vacuum level is regulated so as to not completely collapse the diseased, inelastic airways. The target lung region (TLR) will only partially deflate in response to the vacuum if there are collateral pathways, and soon a volume equilibrium will be reached in which the target lung region (TLR) reaches a volumetric steady state.

From this point forward, the flow being aspirated is entering the isolated target lung region (TLR) from the collateral pathways, for example in the fibrous septum FS. These pathways will allow air inflow from the neighboring lung compartment (NLC). Thus, a convective flow of air is created from the neighboring lung compartment (NLC), through the collateral pathways in the fibrous septum FS, into the target lung region (TLR). This flow has the characteristics of a flow stream or current which can carry a sealing agent into the pathways in the separating septum, as will be described in detail below.

The vacuum level may be dynamic and synchronized with the breath cycle in order to maintain a desired vacuum level during all phases of the patient's breath cycle. Generally the vacuum level is between −5 $cmH_2O$ and −20 $cmH_2O$. The vacuum can also be intermittent, although continuous is preferred in order to maintain a constant flow current through the collateral pathways. Control of the vacuum can be manual or automatic based on feedback from lung using sensors built into the catheter or other sensors monitoring the patient's respiration. The vacuum instrument typically is comprised of a vacuum pump or vacuum source and will usually include, a vacuum regulator with closed loop feedback so that the vacuum output from the instrument is unchanged when conditions at the other end of the catheter change, and the requisite sensors, electronics, power supply and user interface. The vacuum instrument also comprises a particulate trap to intercept and collect any of the agent being administered into the lung, described later.

The applied vacuum fundamentally changes the airflow ventilation dynamics in the affected lung areas. Normally, in the lower airways and lung lobule structures, with or without emphysema, ventilation consists of very small amplitude bidirectional movements of small volumes of air and indeed much of the gas movement can be characterized more accurately by diffusion and not convection. However, once vacuum aspiration is applied, the flow current established by aspiration dominates the flow dynamics in the affected areas and creates a unidirectional convective flow environment. The convective flow is characterized by a static unidirectional flow current and the pre-existing gas diffusion or small bidirectional movements of volume are completely nullified by the convective flow.

Figure 3C:
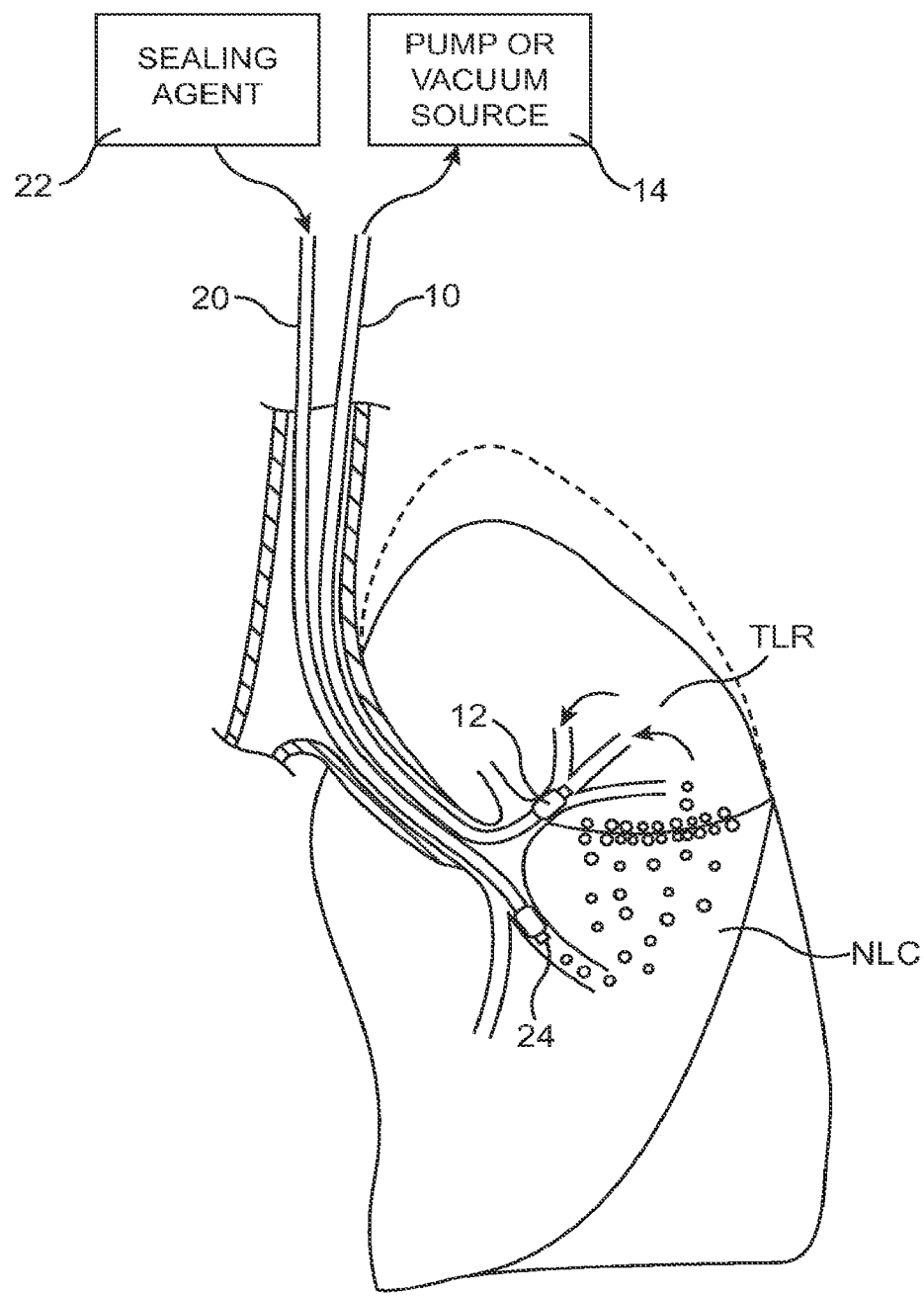

Referring to FIG. 3C, once the convective aspiration flow path is established, an agent delivery catheter 20 is positioned in the bronchi feeding the neighboring lung compartment (NLC). Alternatively, a second lumen contained in the aspiration catheter 10 may be used to deliver the agent into the convective collateral pathways. The agent is entrained into the airflow stream that has been established by the aspiration. The second catheter 20 is illustrated as a balloon catheter but could alternatively be a non-balloon catheter, a wedge catheter, or the like, and could be inserted trans-orally or trans-nasally to the neighboring lung compartment. Optionally, the catheter may be inserted through a bronchoscope or the aspiration catheter. A proximal end of the agent delivery catheter 20 outside the patient is connected to an instrument 22 containing the source of agent and a delivery system to propel it into the agent delivery catheter.

When the user has confirmed that the aspiration flow current has been properly established by analysis of the aspiration parameters such as pressure and flow, the agent delivery instrument 22 is actuated to release and propel the agent. The agent is ejected from a distal tip 24 of the agent delivery catheter 22 into the neighboring lung compartment (NLC) and is readily entrained into convective flow established by the aspiration catheter 10. The delivery of agent will be controlled in order to maximize the chance that the agent will be entrained. For example, the agent may only be delivered during the inspiratory phase of the patient's breath cycle so that the agent is not spread inadvertently to other lung areas during the counter flow which would occur during exhalation. Propulsion of the agent may be designed such that a burst or high velocity mist is ejected from the agent delivery catheter tip at the designated time in order to increase the time-of-flight to help the agent travel distally to regions of greater aspiration current.

Eventually, the agent is drawn into the collateral pathways e.g., in the fibrous septum FS, by the convective current. Initially much of the agent travels through the collateral pathways into the target lung region (TLR) and is collected by the aspiration catheter 10 and evacuated to a particulate trap or other filter at the aspiration instrument. Only some of the agent is initially deposited on the surfaces of the collateral pathways as the agent is flowing with the aspiration current. But as agent becomes deposited, the collateral pathway aperture size is reduced thus increasing the rate of deposition of agent in the pathways and reducing the rate of agent passing through the pathways from the neighboring lung compartment (NLC) into the target lung region (TLR). Eventually no more agent can travel through the pathways as the pathways become occluded due to agent deposition. Analysis of the aspiration parameters will show a change in resistance to aspiration flow indicating that the upstream conditions have changed, namely the resistance of the collateral pathways. Aspiration and or agent delivery parameters such as amplitude, frequency and composition, can be stopped when the desired resistance is met, or can be modulated to arrive at the desired resistance.

The agent that is delivered to increase the resistance of the collateral pathways can be an aerosolized, nebulized or an atomized agent. To increase time-of-flight the agent can be aerosolized, nebulized or atomized at the distal tip of the agent delivery catheter. The agent can be bioresorptive or biodegradeable, non-resorptive or non-biodegradeable, can be inflammatory or non-inflammatory, can be inert or can cause tissue reaction such as fibroblast encapsulation, ossification or calcification.

Suitable agents can be a solid, such as but not limited to a powder, such as silicone or silica, polyethylene glycol (PEG), bone, calcium hydroxylapatite, polyvinylalcohol (PVA), or the like. Alternatively, the agent can be a fluid or liquid such as but not limited to glucose, glycerin, hyaluronic acid, polylactic acid, liquid silicone, perfluorocarbon, or the like. Additional examples of the clogging agent include sucrose or other sugar-type compounds or isomers; celluloic materials, like sodium carboxymethylcellulose; colloids; and crystalloids. In the case of a liquid it is important that the liquid be adequately aerosolized, nebulized or atomized before it is ejected into the lung airways. The agent can be a single component agent, for example talc powder, or can be a composite, for example glucose and talc powder. In the later example glucose can be nebulized or aerosolized to act as a carrier agent carrying the talc powder in a suspension matrix to the site of deposition. Further, when the composite glucose-talc suspension matrix deposits in the collateral pathways and restricts or clogs them, over time the glucose is resorbed into the tissues while the talc stays deposited in the pathways. Similarly the carrier agent can be phagocytized, sloughed off, dissolved or otherwise removed from the lung. Another example of a composite mixture with a carrier agent is calcium hydroxylapatite suspended in a carrier cloud of nebulized sodium carboxymethylcellulose and saline. The agent can also be a substance, again such as glucose, but which has another ingredient chemically bonded to the glucose, thus using glucose as a carrier molecule to deliver the other ingredient to the site of deposition. At the site, the ingredient dissociates from the glucose molecule at over time. For example the chemical bonds may be relatively weak bonds that simply break over time, or as the glucose is chemically altered as a natural part of resorption into the tissue, the bond is broken releasing the ingredient which then stays behind in the collateral pathway. Or the chemical bond may be designed to break when the molecule reacts with the physiological conditions in the lung, such as temperature, hydroxyl groups, carbon dioxide, etc. Or the chemical bond may remain intact until a secondary agent is introduced to react with the molecule and break the bond releasing the ingredient. The secondary agent can be a certain gas introduced at a later time, or an energy source applied to the area as described below.

In a second embodiment, a method and devices are disclosed in which the agent that is delivered is designed to have a state change or undergo chemical alteration after being deposited in the collateral pathway. The state change allows the agent to be delivered in a highly particalized small state in order to maximize time-of-flight and penetration into the collateral pathways. Once deposited, the agent can change to a less particalized state with sufficient persistence to stay at the site of deposition. For example, typical sizes of the particles in the particulate state can have molecular weights of 100-500 Daltons versus molecular weights of 100-1,000 KDa in an agglomerated or coalesced state. The larger size would immobilize the agent onto the host tissue to resistant migration. The particles in the delivered state may also be hydrophobic or lubricious or very light in viscosity and generally highly un-reactive with like particles in order to maximize penetration into the collateral pathways.

Figure 3D:
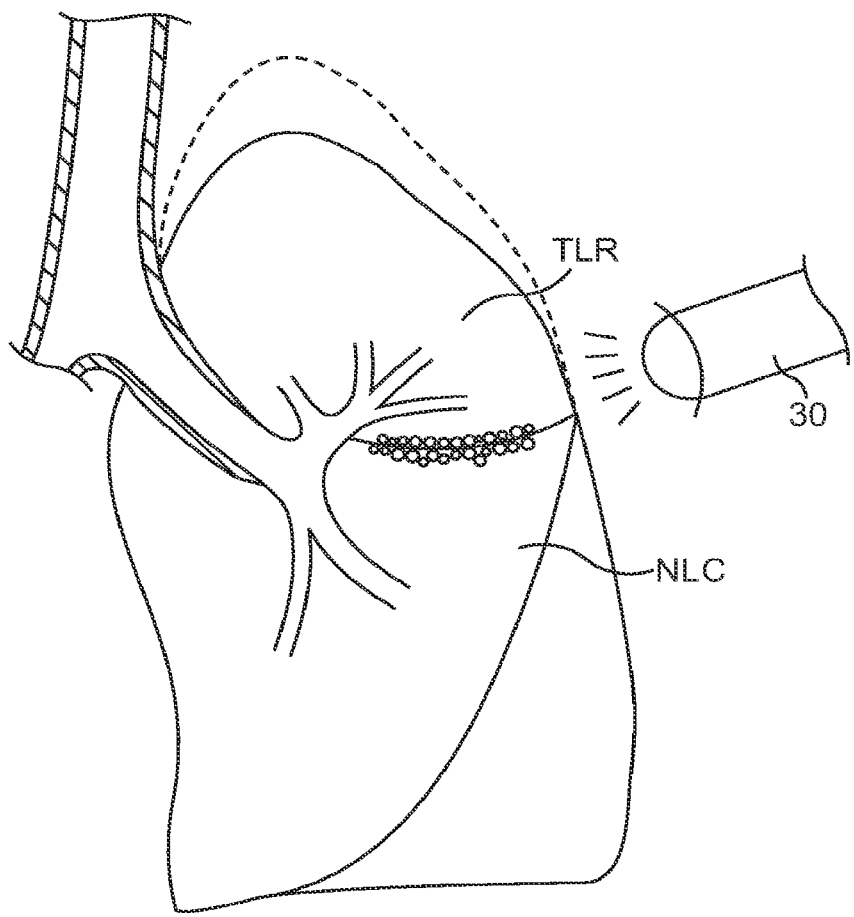

Once at the site of deposition, a state change can convert the agent into a more persistent form having improved clogging behavior. For example, the agent after its state change can react or coalesce with like particles to form large matrices of material, or can become sticky or can become hydrophilic or thicken to a high viscosity. The transformed agent will have improved persistence, for example due to its bulk or due to chemical interaction with the host tissues such as chemical bond forces. Alternatively, the agent could comprise hydroxyl group or other chemical groups which bond to the host tissue surface. In some instances, the agent can be polymerized or otherwise solidified by exposure to activating radiation from a source 30 (FIG. 3D).

Particalization of the agent immediately prior to delivery is accomplished by aerosolizing, nebulizing or atomizing as described earlier. A persistent or coalesced structure may be created after the agent has been deposited in the collateral pathway and could occur automatically for example with a time-delayed reaction designed into the chemical structure. Or, the agent could be designed to react under the physiological conditions existing in the pathway, as described earlier. Alternatively, coalescence could be induced manually, for example, by applying an energy source to the agent. The energy source can be applied endobronchially (such as using a catheter) or from the outside of the patient's body (e.g., using an MRI machine). The energy source can be for example photodynamic energy, light energy, ultrasonic, radiofrequency, electromagnetic, magnetic or any energy source. The energy is preferentially targeted to the area of agent deposition in the collateral pathways and not to surrounding areas that are not part of the pathways. For example, a targeted ultrasonic or other energy beam can be focused on the area much like lithotripsy.

Figure 4A:
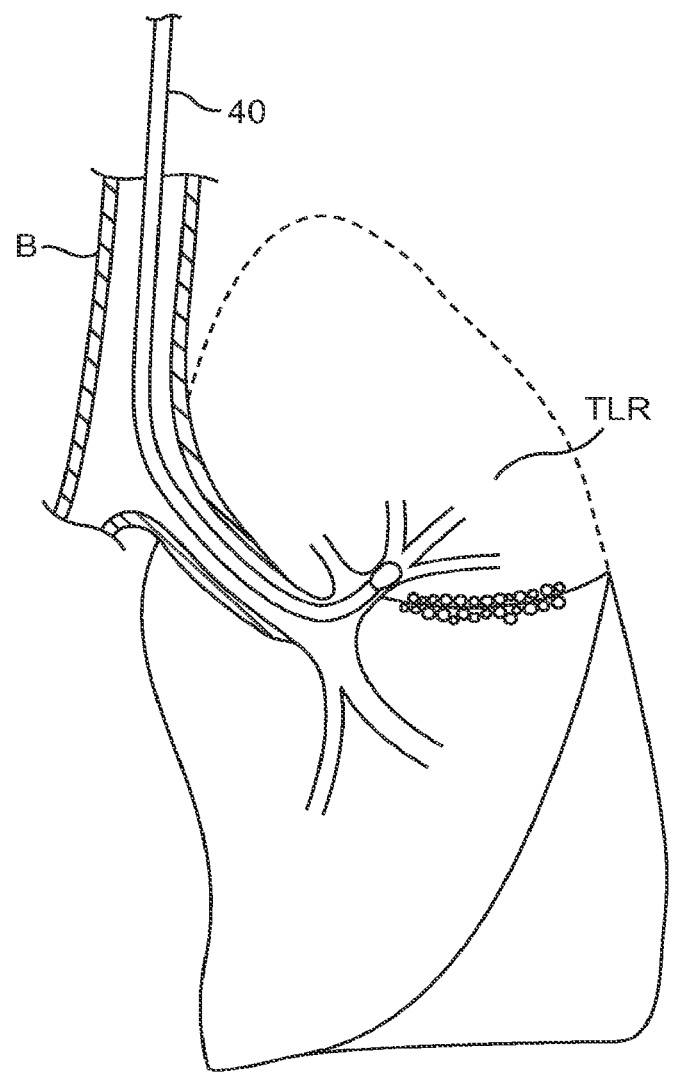
FIGS. 4A and 4B illustrate placement of an occlusive stent to treat the target lung region after the collateral/ventilation pathways have been blocked.
Figure 4B:
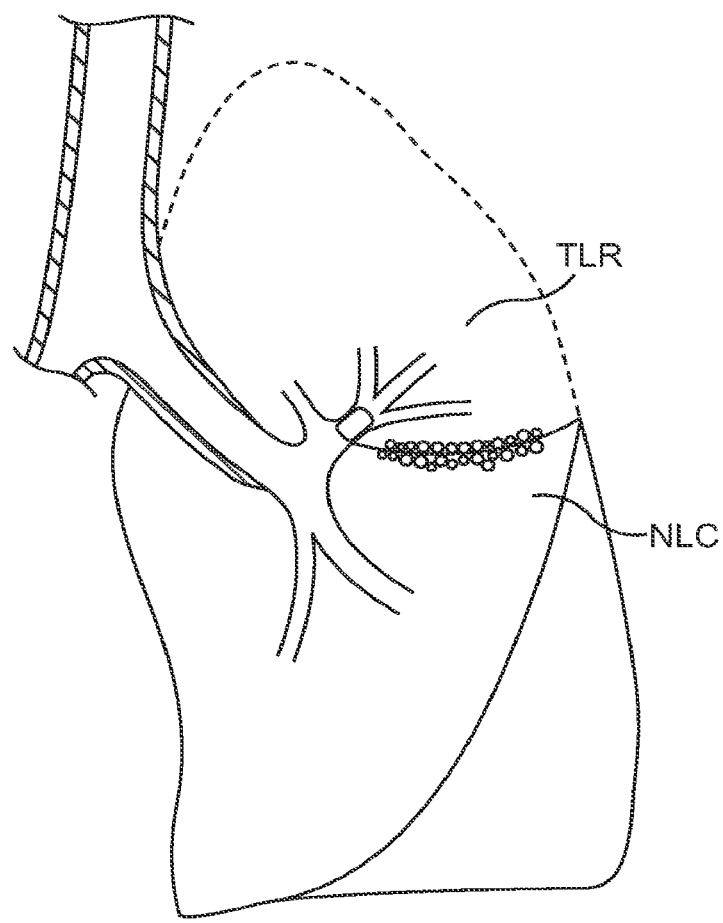

The blocking treatment can be terminated when the flow resistance of the collateral passages has been increased as desired by the user. The agent delivery and the aspiration flow will be terminated, and the agent delivery catheter 20 is removed from the neighboring lung compartment (NLC). Then as illustrated in FIGS. 4A and 4B, the aspiration catheter 10 is removed and an occlusion catheter 40 is inserted into the targeted region. An occlusive stent 42 or other blocking element is then delivered to the feeding bronchus or feeding bronchi of the targeted lung region (TLR). The occlusion catheter 42 is removed as illustrated in FIG. 4B, and the respiratory gases in the targeted region are absorbed over time by a process called absorption atelectasis. Thus the diseased targeted lung region (TLR) is deflated or collapsed and it is not subject to re-inflation through the collateral pathways.

In a further aspect of the present invention, an antidote substance may be delivered to the targeted lung region (TLR) and/or neighboring lung compartment (NLC) in order to dissolve, remove, neutralize or cause resorption of any stray agent that has deposited in undesirable areas. The antidote is delivered via inhalation, aerosolization, nebulization, atomization, or catheter based delivery or lavage.

The present invention thus provides systems and methods for delivery of the agent is that is highly controlled despite the inspiratory and expiratory volume excursions and gas diffusion in the region of interest. In the present invention, unique and novel techniques are employed to control and target the agent delivery; (1) a lung area is definitively diagnosed as requiring treatment for emphysema, (2) that lung area is definitively diagnosed as possessing collateral pathways, (3) an airway is minimally invasively isolated with an isolation catheter, (4) vacuum is applied to a lung region, (5) convective flow is established across a collateral channel, (6) normally present inspiratory and expiratory movements of gas and gas diffusion is canceled out by the convective flow current, (7) agent is introduced into the convective current, (8) the convective current carries the agent to the desired location with negligible losses in other areas, (9) optionally, the agent is activated by chemical reactions or by application of energy from a source to coalesce into a clotting or clogging agent.

It can be appreciated that there are many combinations of the above embodiments that can be combined in different ways for a host of applications. For example, the delivery of the agent can be performed opposite as that described in which aspiration is applied to the neighboring lung compartment (NLC) in which case the agent is delivered into the targeted region. This orientation may be preferred in case some of the agent is inadvertently deposited in unwanted areas; if these areas are in the lung area intended to be collapsed then side effects of the agent can be neglected.

Some additional option configurations of the invention include the catheter configurations, for example, the catheters may or may not include isolation. In various embodiments, the aspiration and agent delivery catheter can be a single multiple lumen catheter, a bifurcated catheter, or two separate catheters. In various embodiments, agent delivery can occur by the patient spontaneously inspiring from a reservoir of agent.

In various embodiments, different or multiple regions of the organ can be treated, simultaneously or sequentially, or regions can have repeat treatments. In various embodiments, the treatment can be acute, lasting only seconds or minutes, or can take a longer period of time, for example days or weeks, in which case there may be required multiple interrupted treatments before the full effect is realized. Certainly, a variety of aspiration vacuum and or agent delivery parameters can be applied, such as different frequencies and amplitudes and concentrations. Emitted dose of agent can be modulated as needed using feedback of the appropriate measured parameter. Agent delivery can be done concurrently with activation or separately.

Navigation and positioning of the catheters can be bronchoscopically or fluoroscopically and catheters can be inserted through the working channel of the bronchoscope or over guide wires or combinations thereof. Placement of the catheters can be bronchoscopically guided and then secured in place with the appropriate means at the distal or proximal end. The bronchoscope can be used during the aspiration and agent delivery or can be removed leaving the aspiration and agent delivery catheters securely positioned in place.

Also, the treatment can be performed using positive pressure by insufflating a target lung region (TLR) with the agent and optionally aspirating it from the neighboring lung compartment (NLC), or visa versa. Or, the agent can be simply instilled into the target area then aspirated back out, either simultaneously or sequentially. Or a differential positive pressure can be created in the system to create the flow current.

In addition, while the above description is directed primarily to a collateral pathway pre-treatment approach as a prerequisite to minimally invasive lung volume reduction for treating emphysema, the collateral pathway treatment may also be applied to other therapeutic or diagnostic procedures, such as tuberculosis treatment, ventilation therapy for ARDS, SARS treatment, CF treatment, cancer treatment, fistula treatment or the like. Additionally, the invention can be applied to other body organ systems with collateral pathways, such as the vascular system, and can be applied to gas filled systems or liquid filled systems. Furthermore, in various embodiments, the collateral pathway treatment can be performed as an outpatient procedure while the patient is spontaneously breathing and properly sedated, or during general anesthesia.

Figure 5:
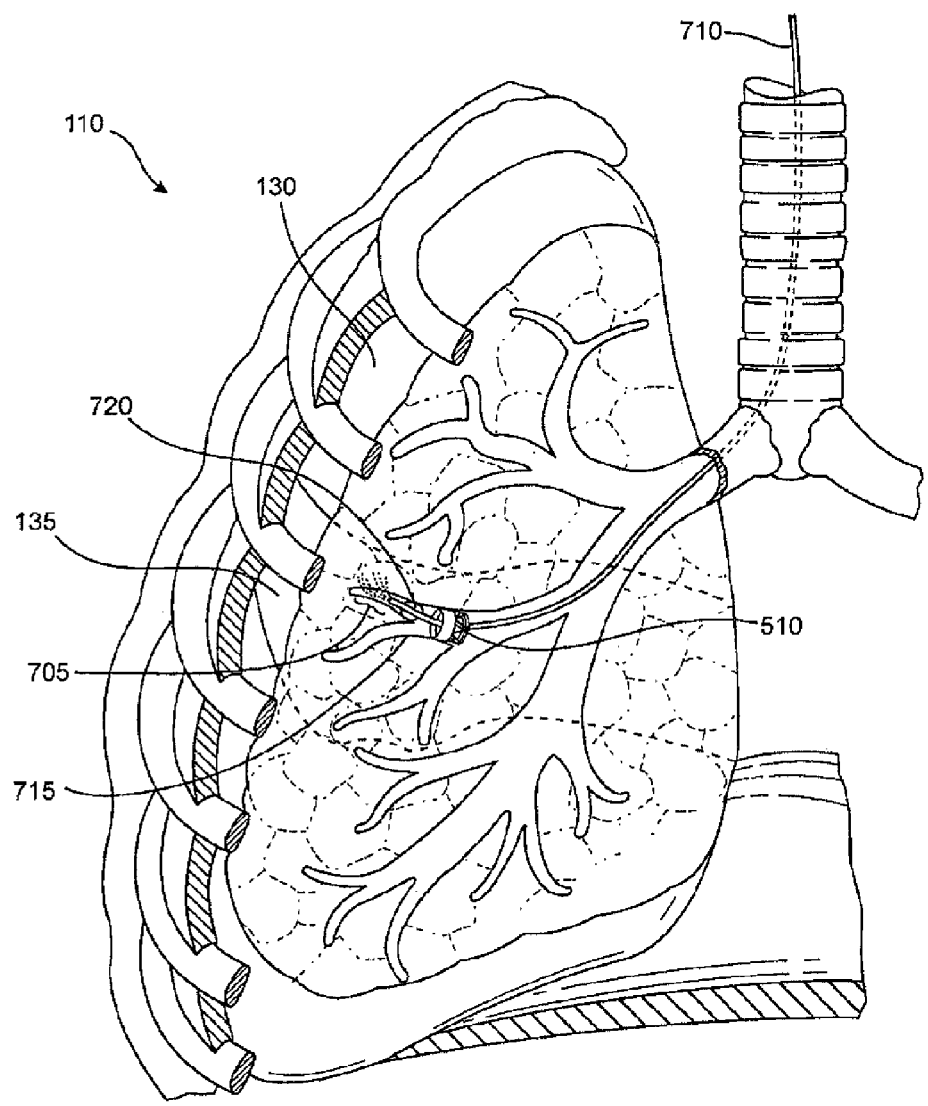
FIG. 5 shows an anterior view of a pair of human lungs and a bronchial tree with a catheter positioned in a bronchial passageway for injecting a therapeutic agent into a target region of the lung.

In another embodiment, and with reference now to FIG. 5, the targeted lung region can be suctioned using a vacuum source through one or more suction catheters that are deployed at or near the targeted lung region. The suction catheter can be used to aspirate fluid from the targeted lung region by applying suction to the proximal end of the catheter, and this suction is transferred to the distal region of the bronchial passageway through the internal lumen of the catheter.

The targeted lung region can be suctioned prior to injection of a therapeutic agent into the targeted lung region in order to remove fluid and either reduce the volume or collapse the targeted lung region. This reduction in volume or collapse of the targeted lung region serves to create space in the targeted lung region for injection of the therapeutic agent. As discussed below, suction can also be used after injection of the therapeutic agent, such as to suction the therapeutic agent from the targeted lung region. If a bronchial isolation device is implanted in the lung, the suction can be performed before the device is implanted or while the device is implanted, such as suctioning through the device. In this regard, the suction can be applied either distally or proximally of the implanted bronchial isolation device.

The suction can be applied either continuously or in a pulsatile manner, such as by using either a continuous or pulsatile vacuum source. In one embodiment, fluid can be aspirated from the targeted lung region using a very low vacuum source over a long period of time, such as one hour or more. In this case, the catheter may be inserted nasally and a water seal may control the vacuum source.

In one embodiment, pulsatile suction is defined as a vacuum source that varies in vacuum pressure from atmospheric pressure down to −10 cm H2O. The frequency of the pulse can be adjusted so that the collapsed bronchus has time to re-open at the trough of the suction wave prior to the next cycle. The frequency of the pulse can be fast enough such that the bronchus does not have time to collapse at the peak of the suction wave prior to the next cycle. The suction force can be regulated such that even at the peak suction, the negative pressure is not low enough to collapse the distal airways.

The frequency of the suction (either pulsatile or continuous) could be set to the patient's respiratory cycle such that negative pressure is applied only during inspiration. That is, the suction is synchronized with the patient's respiration such that continuous suction or a series of suction pulses are applied to the targeted lung region only while the patient is inhaling. This can allow the lung's tethering forces to be exerted thereby keeping the distal airways open.

One possible method of implementing pulsatile suction is to utilize a water manometer attached to a vacuum source. The vacuum regulator pipe in the water manometer can be manually or mechanically moved up and down at the desired frequency to the desired vacuum break point (0 to −10 cm). This is only an exemplary method of creating a pulsatile vacuum source and it should be appreciated that other methods can be used.

A therapeutic agent comprised of a bulking agent can be used to fill space (such as space within the targeted lung region and/or a collateral pathway to the targeted lung region) and thereby partially or entirely seal off collateral flow into the targeted lung region.

Various substances can be used as bulking agents and carriers. Some exemplary substances that can be used as bulking agents and carriers include hydrogel and autologous blood among others. A hydrogel is defined as a colloidal gel in which water is the dispersion medium, and a colloid is defined as a mixture with properties between those of a solution and fine suspension. Hydrogels can be used as implantable bulking agents as well as a carrier for other therapeutic agents as the hydrogel can be designed to be absorbed slowly by the body, thus releasing the therapeutic agent into surrounding tissue over time.

Another approach for blocking collateral flow into a targeted lung region is to inject a bulking agent (such as hydrogel) into the target lung region prior to isolating the targeted lung region with bronchial isolation devices. One method for implanting the bulking agent into the target region is to use a catheter.

FIG. 5 illustrates an example of a method wherein a bulking agent 705 is delivered to a targeted lung region using a delivery catheter 710. The targeted lung region is located in the right middle lobe 135 of the right lung 110. The delivery catheter 710 can be a conventional delivery catheter of the type known to those of skill in the art. The delivery catheter 710 is deployed in a bronchial passageway, such as in the segmental bronchi 715, that leads to the targeted lung region. A bronchial isolation device 510 can optionally be deployed either before or after deployment of the delivery catheter 710 or need not be deployed at all. As mentioned, the targeted lung region can be suctioned prior to injection of the bulking agent.

Once the delivery catheter 710 is deployed in the targeted lung region, the bulking agent 705 can be delivered into the targeted lung region using the delivery catheter 710. This can be accomplished by passing the bulking agent through an internal lumen in the delivery catheter so that the agent exits a hole in the distal end of the delivery catheter 710 into the targeted lung region. As shown in FIG. 5, the distal end of the delivery catheter 710 can be sealed within the targeted lung region by inflating a balloon 720 that is disposed near the distal end of the catheter according to well-known methods. A balloon-tipped catheter is not necessary for use.

In order to track the dispersion of the bulking agent, or any other injected therapeutic agent, a small quantity of radiographic contrast can be mixed with the bulking agent prior to injecting the bulking agent. The extent and spread of the injection can then be monitored with fluoroscopy.

Prior to or after the bulking agent is injected, at least one bronchial isolation device can optionally implanted in the bronchial lumen(s) leading to the targeted lung region in order to restrict direct flow to the targeted tissue through the bronchial lumen, as described above. In this manner, the tissue is fully isolated. However, it should be appreciated that the bronchial isolation device is not required to be implanted in combination with use of the bulking agent. It should be appreciated that other methods of delivering the bulking agent to the target location are possible.

A number of embodiments of the invention have been described. Nevertheless, various modifications may be made without departing from the spirit and scope of the invention. Accordingly, other embodiments are within the scope of the following claims.

What is claimed is:

1. A method of regulating air flow for a targeted lung region comprising a segment or lobe of the lung, the method comprising:
   selecting a patient having a collateral pathway in the lung;
   providing a mixture comprising autologous blood into lung tissue over a period of time;

reducing collateral air flow that flows through the collateral pathway between the targeted lung region and another segment or lobe of the lung by injecting the mixture into the targeted lung region; and after reducing collateral flow to the targeted lung region, reducing direct air flow in a bronchus that provides direct air flow to the targeted lung region.

2. The method of claim 1, wherein the injecting comprises:

deploying a delivery catheter through a bronchial tree into the targeted lung region such that a distal end of the delivery catheter communicates with the targeted lung region;

flowing the mixture through the delivery catheter so that the mixture exits the distal end of the delivery catheter into the targeted lung region.

3. The method of claim 1, wherein the mixture further comprises a sclerosing agent that induces a reaction that causes sclerosis in the lung tissue.

4. The method of claim 3, wherein the sclerosing agent is selected from the group consisting of tetracycline, doxycycline, and minocycline.

5. The method of claim 1, wherein reducing direct flow comprises implanting a flow control element which allows air flow in an exhalation direction and restricts air flow in an inspiration direction.

6. The method of claim 4, wherein reducing direct flow comprises implanting a flow control element which allows air flow in an exhalation direction and restricts air flow in an inspiration direction.

7. The method of claim 1, wherein the mixture further comprises a bulking agent, wherein the bulking agent is configured to cause the mixture to be released into tissue of the target lung region over a period of time.

8. The method of claim 1, wherein the mixture further comprises radiographic contrast.

* * * * *